United States Patent [19]

Jenkins, Jr. et al.

[11] 4,405,338
[45] Sep. 20, 1983

[54] EXTENDED AVIATION JET FUEL STABILIZED WITH PHENOALDEHYDE AMINE DERIVATIVES

[75] Inventors: Robert H. Jenkins, Jr., Walden; William M. Sweeney, Wappingers Falls, both of N.Y.

[73] Assignee: Texaco Inc., White Plains, N.Y.

[21] Appl. No.: 345,878

[22] Filed: Feb. 4, 1982

[51] Int. Cl.³ .................. C10L 1/24; C07C 87/28
[52] U.S. Cl. .............................. 44/78; 252/404; 44/76
[58] Field of Search ......... 44/77, 78, 76; 252/404; 564/390; 208/11 LE, 11 R, 14, 15, 17

[56] References Cited

U.S. PATENT DOCUMENTS

| | | | |
|---|---|---|---|
| 3,234,285 | 2/1966 | Moss et al. | 44/78 |
| 3,326,800 | 6/1967 | Coffield et al. | 252/404 |
| 3,591,637 | 7/1971 | O'Shea et al. | 564/390 |
| 3,960,758 | 6/1976 | Witte et al. | 252/404 |
| 4,071,433 | 1/1978 | Hanson | 208/11 LE |
| 4,322,304 | 3/1930 | Parlman et al. | 252/404 |

Primary Examiner—Charles F. Warren
Assistant Examiner—Y. Harris-Smith
Attorney, Agent, or Firm—Carl G. Ries; Robert A. Kulason; Carl G. Seutter

[57] ABSTRACT

Avjet fuel, extended with shale oil distillate boiling in the diesel fuel boiling range, is improved with respect to thermal stability by addition of 0.2 w % of

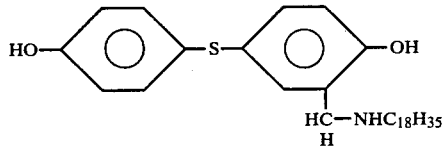

23 Claims, No Drawings

EXTENDED AVIATION JET FUEL STABILIZED WITH PHENOALDEHYDE AMINE DERIVATIVES

FIELD OF THE INVENTION

This invention relates to certain additives which improve the thermal stability of hydrocarbon fuels including those which have been extended by non-petroleum distillate.

BACKGROUND OF THE INVENTION

As is well known to those skilled in the art, hydrocarbon fuels such as aviation jet fuels are expensive and may become in short supply as supplies of crude oil become more difficult to obtain. Attempts to extend these fuels by addition thereto of non-petroleum distillates, such as those derived from shale oil, tar sands, H-oil etc., have been unsatisfactory because the extended fuels have decreased thermal stability as measured by ASTM D 3241 - the JFTOT Test.

It is also known that it is desirable to improve the stability with respect to oxidation at elevated temperatures of other hydrocarbon fuels which may have a thermal stability rating of unsatisfactory or satisfactory.

STATEMENT OF THE INVENTION

In accordance with certain of its aspects, this invention is directed to the method of improving the thermal stability of a hydrocarbon fuel heavier than gasoline which comprises mixing (i) a major portion of a hydrocarbon fuel heavier than gasoline and (ii) a minor thermal stability-improving amount of, as a thermal stability-improving additive,

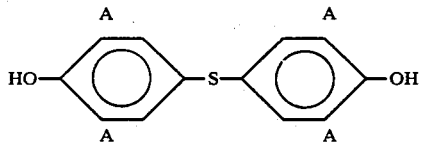

wherein A is hydrogen or

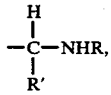

R is a primary or secondary $C_4$-$C_{20}$ alkyl, cycloalkyl, or alkenyl hydrocarbon group, and R' is hydrogen or a $C_1$-$C_4$ alkyl hydrocarbon group, and at least one A is other than hydrogen thereby forming a hydrocarbon fuel product of improved thermal stability; and recovering said product.

In accordance with certain of its other aspects, this invention is directed to

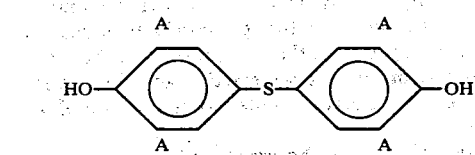

wherein A is hydrogen or

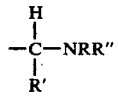

R is a primary or secondary $C_4$-$C_{20}$ alkyl cycloalkyl, or alkenyl hydrocarbon group, R' is hydrogen or a $C_1$-$C_4$ alkyl hydrocarbon group, R" is hydrogen or selected from the same group as that from which R is selected and at least one A is other than hydrogen.

DESCRIPTION OF THE INVENTION

The charge hydrocarbon fuels which may be treated by the process of this invention may include those compositions generally identified as being heavier than gasoline, commonly including jet fuel, aviation jet fuel (Avjet fuel), kerosene, diesel oil, etc.

These fractions may typically have an ibp of 250° F.–500° F., preferably 300° F.–400° F., say 375° F. an ep of 500° F.–700° F., preferably 500° F.–600° F., say 525° F. and an API gravity of 25–70, preferably 40–50, say 42. These compositions may typically contain a wide range of additives including corrosion inhibitors, etc.

A typical hydrocarbon fuel which may be treated by the process of this invention may be an Avjet A fuel having the characteristics set forth in Table I infra.

Although the thermal stability (JFTOT) of these hydrocarbon fuels may be improved by the technique of this invention, it is found that the technique of this invention is particularly useful when hydrocarbon fuels have been extended as by non-petroleum distillates.

These hydrocarbon fuels may be extended by addition thereto of various non-petroleum distillates typified by (i) shale oil distillate (32.6 API) boiling in the diesel fuel range of 530° F.–678° F., (ii) a tar and distillate (35 API) having an ibp of 380° F. and an ep of 590° F., (iii) an H-oil distillate (38.9 API) having an ibp of 400° F. and an ep of 620° F. prepared by thermally cracking a residual fuel followed by hydrocracking and thereafter distillation; etc.

A typical preferred extender may be the Paraho Shale Diesel Oil Distillate set forth in Table I.

TABLE I

|  | AVJET A Gasoline | Paraho Shale Diesel Oil |
|---|---|---|
| Gravity AP | 42.4 | 32.6 |
| ASTM Distillation °F. |  |  |
| 10% | 376 | 530 |
| 30% | 400 | 568 |
| 50% | 423 | 593 |
| 90% | 486 | 659 |
| 95% | 504 | 676 |
| Ep | 526 | 678 |
| Flash Point °F. | 129 | 184 |
| Cloud °F. | −56 | unsuitable |
| Pour Point °F. | −55 | 50 |
| Cetane | 43.0 | 62.8 |
| Kin. Vis. cs (40° C.) | 1.50 | 5.30 |
| % S (x-ray) | 0.040 | 0.58 |
| JFTOT (400° F.) |  |  |
| D-3241 | 2 | 4 |

The extender may be added to the hydrocarbon fuel in amount of 0–20 w %, preferably 5–15 w %, say 10 w % of the total of the extender plus fuel.

Although these compositions may be satisfactory from the point of view of combustion properties (including boiling range, viscosity, cetane number, etc.), it is found that they are undesirably characterized by poor resistance to oxidation as measured by modified ASTM-D 3241, the JFTOT Test carried out at 400° F. rather than at the standard 500° F. In this test, a rating of 0 is good, 4+ is bad and a rating less than 3 is a satisfactory rating. A satisfactory Avjet fuel may commonly have a rating of 2+. The same jet fuel in a 90–10 vol % mixture with a Paraho Shale Diesel Distillate fuel may have a JFTOT rating of 4+ which is unsatisfactory.

In accordance with practice of the process of this invention, there may be added to the fuel composition a minor thermal stability-improving amount of a thermal stability-improving additive. Preferably the additive is added in an amount of 0.01–2 w %, more preferably 0.1–1 w %, say 0.2 w % of the total of the extended composition.

The thermal stability-improving additive or agent of this invention may include those of the formula

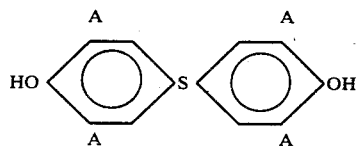

wherein A is hydrogen or

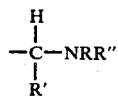

R is a primary or secondary $C_4$–$C_{20}$ alkyl, alkenyl, or cycloalkyl hydrocarbon group, R" is hydrogen or selected from the same group as that from which R is selected, R' is hydrogen or a $C_1$–$C_4$ alkyl hydrocarbon group, and at least one of the A substituents is other than hydrogen.

The phenyl rings may bear inert substituents, which do not interfere with preparation of the additive, typified by —OH groups, by lower ($C_1$–$C_4$) alkyl hydrocarbon groups, etc. These inert substituents may occupy the positions meta- to the —OH groups designated in the formula above or the positions shown by less than all of the A groups. One ring may have an SH group in place of the OH group shown; in this case, the A substituents will be on the ring bearing the OH group.

Illustrative additives or agents may include those set forth in the following table, the first listed being preferred.

TABLE

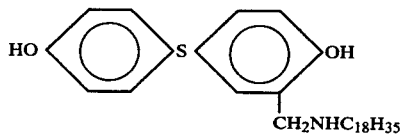

N—(3-[4-hydroxythiophenoxy]-6-hydroxybenzyl)oleyl amine

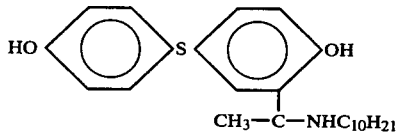

TABLE-continued

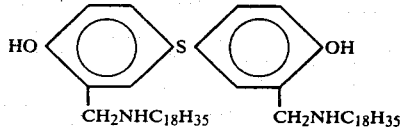

III

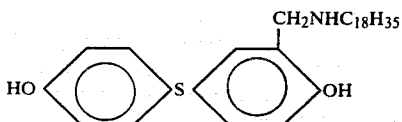

IV

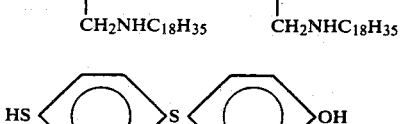

V

VI

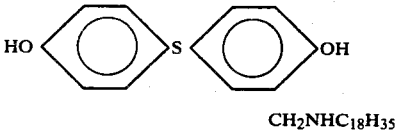

VII

Preparation of the novel additive compounds of this invention may be carried out by reacting (i) a phenol

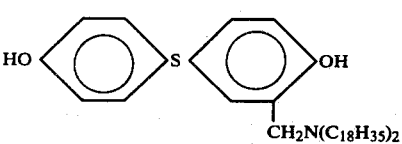

(ii) a primary or secondary $C_4$–$C_{20}$ alkyl or alkenyl or cycloalkyl amine

RNHR"

and (iii) formaldehyde or a $C_1$–$C_5$ alkyl aldehyde

R'CHO in liquid phase preferably in the presence of inert solvent at 60° C.–100° C. thereby forming the desired product.

It is possible to prepare the novel products of this invention by the reaction of (i) a Schiff base formed from the reaction of the amine and the aldehyde and (ii) the phenol or by adding three components simultaneously or in any order. Although satisfactory results may be achieved by adding the components to the reaction vessel in any order, it is preferred to add the phenol last. Preferably the amine is added first and the aldehyde second.

The amines which may be employed in practice of the process of this invention may include primary or secondary amines RNHR" wherein one of R and R"

may be hydrogen. R is a $C_4$–$C_{20}$ alkyl, alkenyl, or cycloalkyl hydrocarbon group. When R is alkyl, it may for example be butyl, amyl, hexyl, octyl, decyl, dodecyl, octadecyl, etc. When R is alkenyl, it may typically be butenyl, pentenyl, oleyl, etc. When R is cycloalkyl, it may typically be cyclohexyl, etc. R" may be hydrogen or it may be selected from the same group as that from which R is selected.

Illustrative amines which may be employed may include the following, the first mentioned being preferred:

TABLE oleyl amine
n-butyl amine
n-octyl amine
2-ethylhexyl amine
cyclohexyl amine
di-n-butyl amine
butyl, octyl amine
di-cyclohexyl amine etc.

The aldehydes which may be employed in practice of the process of this invention may include formaldehyde or $C_1$–$C_5$ alkyl aldehydes R'CHO wherein R' may typically be methyl, ethyl, propyl, isopropyl, n-butyl, t-butyl, sec-butyl, n-amyl, etc. Illustrative aldehydes may include the following, the first mentioned being preferred:

TABLE formaldehyde (as paraformaldehyde)
acetaldehyde
propionaldehyde
butyraldehyde etc.

The phenols which may be employed in practice of the process of this invention may include those having the formula

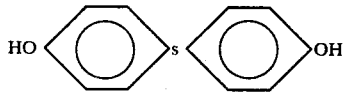

In this formula, as in the others, the reactants may bear inert substituents, and where an atom is shown as having its valence bonds unfilled, these may typically be filled with hydrogen or an inert substituent.

In the case of the phenol, the substituents may include —OH groups preferably meta- to the —OH groups shown in the formula.

Illustrative phenols may include those listed in the following table, the first mentioned being preferred:

TABLE

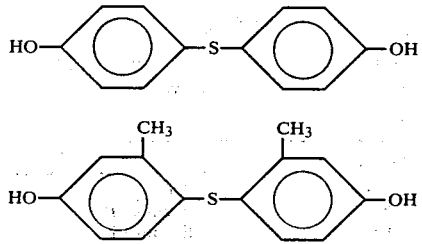

TABLE-continued

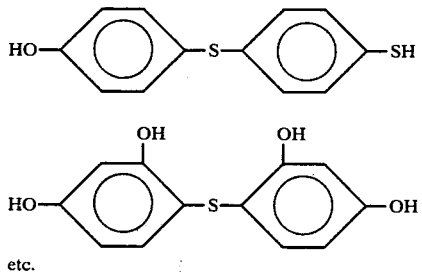

etc.

Reaction may be carried out in inert reaction medium, typically solvents including hydrocarbons such as xylene, or alcohols such as methanol or ethanol. A preferred solvent may be 4:1 (volume) mixture of methanol and xylene. Solvent may typically be present in amounts of 100–1000 parts, say 200 per 100 parts parts of reactants.

Reaction is typically carried out in liquid phase at pressure of 0–100 psig, say atmospheric pressure and 50° C.–200° C., say about 70° C. A preferred reaction temperature may be the reflux temperature of the solvent.

The amine and the aldehyde are preferably employed in substantially equimolar quantities, and this molar quantity may be the same as, or twice, or three times, or four times the molar quantity of the phenol—depending upon the number of nitrogen-containing groups to be introduced to the molecule. When formaldehyde is employed in the preferred embodiment (as paraformaldehyde), the molar quantity is considered to be that corresponding to the molecular weight of formaldehyde.

In accordance with practice of the process of this invention, there may be added to the reaction vessel the amine and the aldehyde together with solvent—preferably a 2:1 (volume) mixture of methanol and xylene. The phenol, preferably dissolved in methanol, is added to the reaction mixture over 5–60 minutes, say 10 minutes with agitation and the reaction mixture is refluxed at 50° C.–150° C., say 70° C. for 4–6 hours, say 5 hours.

During refluxing, the following typical reaction may occur

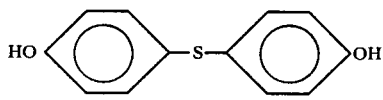

+

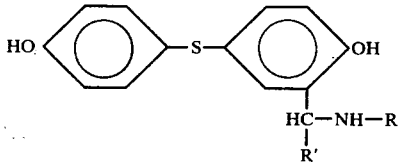

or in a particular instance

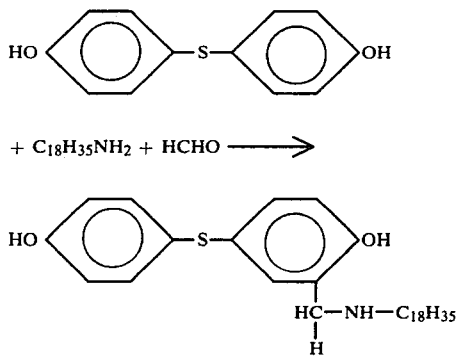

+ C₁₈H₃₅NH₂ + HCHO ⟶

Work-up of the reaction mixture (typically a clear liquid) may be effected by cooling, filtration, and stripping to remove solvents. The product may be used as so recovered with no further treatment. It may be analyzed for molecular weight, total base number, and w % nitrogen.

For convenience in further handling, it may be desirable to dissolve the product in hydrocarbon solvents, typically xylene, gasoline, etc. or in alcohol, typically methanol, ethanol, etc.—depending upon the ultimate use.

It is a feature of this invention that the novel products so prepared may be useful as thermal stability additives in hydrocarbon fuels.

DESCRIPTION OF PREFERRED EMBODIMENTS

Practice of the process of this invention may be apparent to those skilled in the art from the following examples wherein, as elsewhere in this specification, all parts are parts by weight unless otherwise specified. All valence bonds not otherwise filled may be filled with hydrogen atoms or other inert substituents.

EXAMPLE I

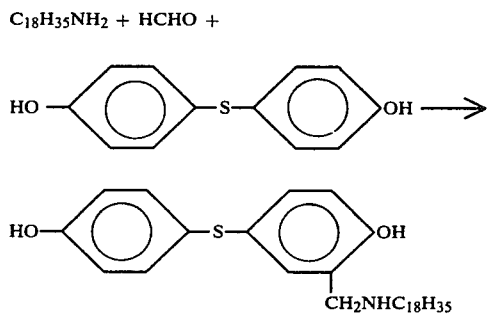

Into a reaction vessel there is added 119 g (0.45 mole) of Armeen OL brand of oleyl amine, 13.5 g (0.45 mole) of paraformaldehyde, 200 ml of anhydrous methanol, and 100 ml of xylene. There are then added with agitation 98.3 g (0.45 mole) of 4,4'-thiodiphenol in 200 ml of methanol.

The reaction mixture is refluxed for 5 hours to give a clear product which is cooled, filtered, and stripped (on a rotary evaporator) of solvent. Analysis reveals molecular weight of 627, TBN (Total Basic Nitrogen) of 105.3, and nitrogen content of 2.80 w %.

Results comparable to those of Example I may be obtained if the amine is:

TABLE

| Example | Amine |
|---|---|
| II | n-butyl amine |
| III | n-octyl amine |
| IV | 2-ethylhexyl amine |

Results comparable to those of Example I may be obtained if the aldehyde is:

TABLE

| Example | Aldehyde |
|---|---|
| V | acetaldehyde |
| VI | propionaldehyde |
| VII | n-butyraldehyde |

Results comparable to those of Example I may be obtained if the phenol is:

TABLE

| Example | Phenol |
|---|---|
| VIII | HO—⟨⟩—S—⟨⟩—OH |
| IX | HO—⟨⟩—S—⟨⟩—SH |
| X | HO—⟨⟩—S—⟨⟩(OH)—SH |

Results comparable to Example I may be obtained if the mole ratio of phenol:aldehyde:amine is:

TABLE

| Example | Mole Ratio |
|---|---|
| XI | 1:2:2 |
| XII | 1:3:3 |
| XII | 1:4:4 |

Clearly however the products of Examples XI, XII, and XIII will contain respectively 2, 3, and 4 nitrogen-containing groups.

EXAMPLE XIV

In this example, there is formed an extended Avjet fuel by mixing 90 vol % of the modified Avjet fuel of Table I and 10 vol % of the Paraho Shale Diesel Oil of Table I. When subjected to the JFTOT Test, this fuel has a rating of 4+ which is unsatisfactory.

On addition to this mixture of 0.2 w % of the reaction product of Example I, the modified JFTOT rating is 2+ which is satisfactory.

EXAMPLES XV–XVII

Results comparable to that of Example XIV may be obtained if the additive is as follows:

| Example | Additive of |
|---|---|
| XV | Example II |
| XVI | Example III |
| XVII | Example IV |

Results comparable to that of Example XIV may be obtained if the fuel is as follows:

| Example | Fuel |
|---------|------|
| XVIII | 95 v % avjet fuel - 2 v % H-oil distillate |
| XIX | 98 v % avjet fuel - 2 v % tar sand distillate |
| XX | 90 v % avjet fuel - 5 v % H-oil distillate |
| | 5 v % tar sand distillate |

Although the additives of this invention may particularly find use as additives to fuel systems which are characterized by bad ratings on the JFTOT Test, it may also be possible to improve a fuel which may have a satisfactory rating.

Although this invention has been illustrated by reference to specific embodiments, it will be apparent to those skilled in the art that various changes and modifications may be made which clearly fall within the scope of this invention.

We claim:

1. The method of improving the thermal stability of a hydrocarbon fuel heavier than gasoline which comprises
mixing (i) a major portion of a hydrocarbon fuel heavier than gasoline and (ii) a minor thermal stability-improving amount of, as a thermal stability-improving additive,

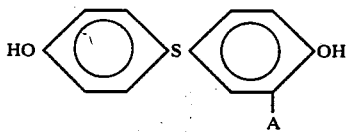

wherein A is

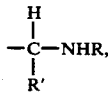

R is a primary or a secondary $C_4$–$C_{20}$ alkyl, cycloalkyl, or alkenyl hydrocarbon group, and R' is hydrogen or a $C_1$–$C_4$ alkyl hydrocarbon group, thereby forming a hydrocarbon fuel product of improved thermal stability; and
recovering said product.

2. The method of improving the thermal stability of a hydrocarbon fuel heavier than gasoline as claimed in claim 1 wherein said additive is

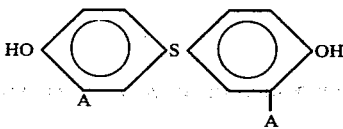

3. The method of improving the thermal stability of a hydrocarbon fuel heavier than gasoline as claimed in claim 1 wherein said additive is

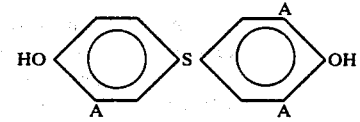

4. The method of improving the thermal stability of a hydrocarbon fuel heavier than gasoline as claimed in claim 1 wherein said additive is

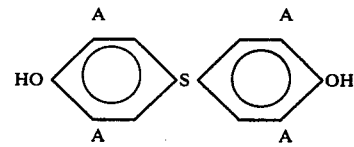

5. The method of improving the thermal stability of a hydrocarbon fuel heavier than gasoline as claimed in claim 1 wherein said additive is the reaction product of (a) a primary or secondary alkyl, cycloalkyl, or alkenyl amine, (b) formaldehyde or a $C_1$–$C_4$ alkyl aldehyde, and (c)

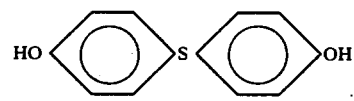

6. The method of improving the thermal stability of a hydrocarbon fuel heavier than gasoline which has been extended by addition of a non-petroleum distillate which comprises
mixing (i) a major portion of a hydrocarbon fuel heavier than gasoline which has been extended by addition of a non-petroleum distillate and (ii) a minor thermal stability-improving amount of, as a thermal stability-improving additive, the reaction product of (a) a primary or secondary alkyl, cycloalkyl, or alkenyl amine, (b) formaldehyde or a $C_1$–$C_4$ alkyl aldehyde, and (c)

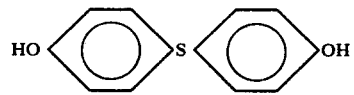

7. The method of improving the thermal stability of a hydrocarbon fuel heavier than gasoline which has been extended by addition of a non-petroleum distillate as claimed in claim 6 wherein said hydrocarbon fuel is an aviation jet fuel.

8. The method of improving the thermal stability of a hydrocarbon fuel heavier than gasoline which has been extended by addition of a non-petroleum distillate as claimed in claim 6 wherein said hydrocarbon fuel is Avjet A fuel.

9. The method of improving the thermal stability of a hydrocarbon fuel heavier than gasoline which has been extended by addition of a non-petroleum distillate as claimed in claim 6 wherein said non-petroleum distillate is a shale oil distillate.

10. The method of improving the thermal stability of a hydrocarbon fuel heavier than gasoline which has been extended by addition of a non-petroleum distillate as claimed in claim 6 wherein said non-petroleum distillate is a shale oil distillate boiling in the diesel fuel boiling range.

11. The method of improving the thermal stability of a hydrocarbon fuel heavier than gasoline which has been extended by addition of a non-petroleum distillate as claimed in claim 6 wherein said non-petroleum distillate is present in amount of 5–20 w % of the total of said hydrocarbon fuel and said non-petroleum distillate.

12. The method of improving the thermal stability of a hydrocarbon fuel heavier than gasoline which has been extended by addition of a non-petroleum distillate as claimed in claim 6 wherein said additive is

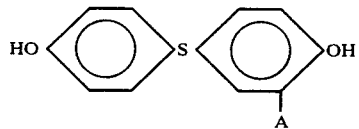

wherein A is

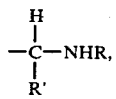

R is a primary or secondary $C_4$–$C_{20}$ alkyl, cycloalkyl, or alkenyl hydrocarbon group, and R' is hydrogen or a $C_1$–$C_4$ alkyl hydrocarbon group, thereby forming a hydrocarbon fuel product of improved thermal stability; and recovering said product.

13. The method of improving the thermal stability of a hydrocarbon fuel heavier than gasoline which has been extended by addition of a non-petroleum distillate as claimed in claim 6 wherein said additive is

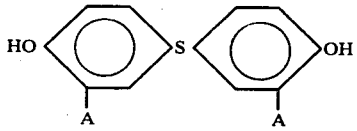

wherein A is

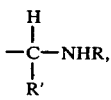

R is a primary or secondary $C_4$–$C_{20}$ alkyl, cycloalkyl, or alkenyl hydrocarbon group, and R' is hydrogen or a $C_1$–$C_4$ alkyl hydrocarbon group, thereby forming a hydrocarbon fuel product of improved thermal stability; and recovering said product.

14.

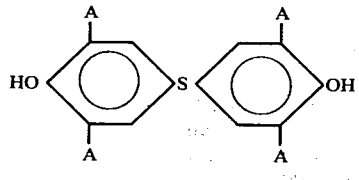

wherein A is hydrogen or

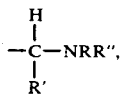

R is a primary or secondary $C_4$–$C_{20}$ alkyl, cycloalkyl, or alkenyl hydrocarbon group, R' is hydrogen or a $C_1$–$C_4$ alkyl hydrocarbon group, R'' is hydrogen or selected from the same group as that from which R is selected, and at least one A is other than hydrogen.

15.

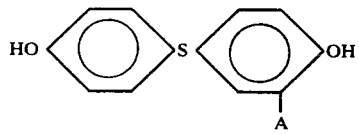

wherein A is

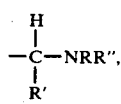

R is a primary or secondary $C_4$–$C_{20}$ alkyl, cycloalkyl, or alkenyl hydrocarbon group, and R' is hydrogen or a $C_1$–$C_4$ alkyl hydrocarbon group and R'' is hydrogen or selected from the same group as that from which R is selected.

16.

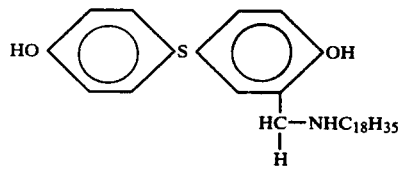

17. The method of preparing product

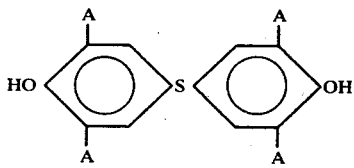

wherein
A is hydrogen or

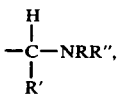

at least one of the A substituents is other than hydrogen,
R is a primary or secondary $C_4$–$C_{20}$ alkyl, cycloalkyl, or alkenyl hydrocarbon group,
R' is hydrogen or a $C_1$–$C_4$ alkyl hydrocarbon group,
R'' is hydrogen or selected from the same group as that from which R is selected, which comprises reacting (a) a primary or secondary alkyl, cycloalkyl, or alkenyl amine, (b) formaldehyde or a $C_1$–$C_4$ alkyl aldehyde, and (c)

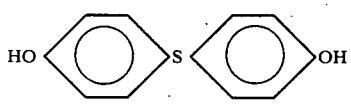

18. The method of preparing product

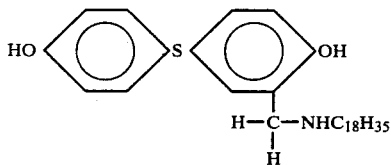

which comprises reacting substantially equimolar portions of formaldehyde, as paraformaldehyde, oleyl amine, and 4,4'-thiodiphenol thereby forming said product; and recovering said product.

19. A hydrocarbon fuel of improved thermal stability which comprises
a major portion of a hydrocarbon fuel heavier than gasoline, and
a minor thermal stability improving amount of, as a thermal stability-improving additive

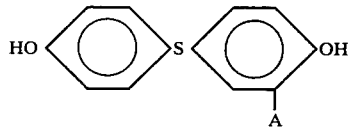

wherein A is

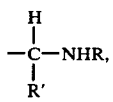

R is a primary or secondary $C_4$–$C_{20}$ alkyl, cycloalkyl, or alkenyl hydrocarbon group, and R' is hydrogen or a $C_1$–$C_4$ alkyl hydrocarbon group.

20. A hydrocarbon fuel as claimed in claim 19 wherein said additive is

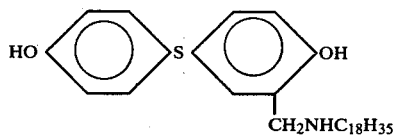

21. A hydrocarbon fuel as claimed in claim 19 wherein said additive is present in amount of 0.01–2 w % of the hydrocarbon fuel.

22. A hydrocarbon fuel as claimed in claim 19 wherein said hydrocarbon fuel has been extended with a non-petroleum distillate.

23. A hydrocarbon fuel composition heavier than gasoline comprising
80–95 parts of hydrocarbon fuel heavier than gasoline
5–20 parts of non-petroleum distillate; and
0.01–2 parts of

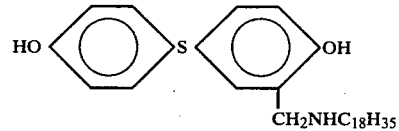

* * * * *